United States Patent
Skiffington et al.

(10) Patent No.: US 10,988,720 B1
(45) Date of Patent: *Apr. 27, 2021

(54) PEEL PLATE ASSEMBLY

(71) Applicants: Richard Skiffington, North Reading, MA (US); Robert Markovsky, Brentwood, NH (US); Byron D. Roberts, Wakefield, MA (US); Stanley E. Charm, Boston, MA (US); Benjamin Mathieu, Hooksett, NH (US); Robert S. Salter, Reading, MA (US)

(72) Inventors: Richard Skiffington, North Reading, MA (US); Robert Markovsky, Brentwood, NH (US); Byron D. Roberts, Wakefield, MA (US); Stanley E. Charm, Boston, MA (US); Benjamin Mathieu, Hooksett, NH (US); Robert S. Salter, Reading, MA (US)

(73) Assignee: Charm Sciences, Inc., Lawrence, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 14/935,692

(22) Filed: Nov. 9, 2015

(51) Int. Cl.
  *C12M 1/00* (2006.01)
  *C12M 1/32* (2006.01)
  *C12M 1/12* (2006.01)

(52) U.S. Cl.
  CPC ............ *C12M 23/12* (2013.01); *C12M 23/20* (2013.01); *C12M 23/38* (2013.01); *C12M 25/06* (2013.01)

(58) Field of Classification Search
  CPC ...... C12M 23/12; C12M 23/38; C12M 23/20; C12M 25/06
  USPC .............................. 435/289.1, 305.1
  See application file for complete search history.

(56) References Cited

U.S. PATENT DOCUMENTS

| | | | |
|---|---|---|---|
| 4,440,301 A * | 4/1984 | Intengan | B01L 3/508 206/456 |
| 4,565,783 A * | 1/1986 | Hansen et al. | C12Q 1/04 435/30 |
| 5,694,478 A | 12/1997 | Braier et al. | |
| 7,452,711 B2 * | 11/2008 | Daykin | C12M 23/10 435/288.3 |
| 7,901,933 B2 | 3/2011 | Green et al. | 435/287.9 |
| 7,957,575 B2 | 6/2011 | Plumb et al. | 382/133 |
| 8,094,916 B2 | 1/2012 | Graessle et al. | 382/133 |
| 8,260,026 B2 | 9/2012 | Plumb et al. | 382/133 |
| 8,417,014 B2 | 4/2013 | Bolea | 382/133 |
| 8,579,080 B2 | 11/2013 | Angelico | 435/287.3 |
| 8,588,505 B2 | 11/2013 | Bolea | 382/133 |
| 2006/0166305 A1 | 7/2006 | Jiang et al. | |

(Continued)

FOREIGN PATENT DOCUMENTS

WO  WO2012176751  12/2012

*Primary Examiner* — Liban M Hassan
(74) *Attorney, Agent, or Firm* — MacCord Mason PLLC

(57) ABSTRACT

Peel plates and plate assemblies are shown and described. In one embodiment, a peel plate assembly includes a semi-rigid plate, a removable cover seal, and an adhesive to provide a moisture vapor barrier. In particular embodiments, the moisture vapor barrier provides less than about one pound peel adhesion and a stiffness for reapplication without wrinkling. The result is a peel plate, assembly, and method for the enumerating a microorganism, when present, in a sample.

8 Claims, 9 Drawing Sheets

(56) References Cited

U.S. PATENT DOCUMENTS

| 2009/0141345 | A1 | 6/2009 | Tsuchiya | |
|---|---|---|---|---|
| 2012/0107913 | A1* | 5/2012 | Baba | C12N 1/00 |
| | | | | 435/243 |
| 2012/0121543 | A1 | 5/2012 | Teather et al. | 424/93.2 |
| 2012/0123003 | A1* | 5/2012 | Otsuka | C08J 3/24 |
| | | | | 521/89 |

* cited by examiner

PEEL PLATE ASSEMBLY

FIELD OF THE TECHNOLOGY

The present disclosure relates generally to analytical testing, and more particularly to improved peel plate assemblies and devices.

BACKGROUND

It is desirable to provide rapid, effective detection and identification of various and numerous microorganisms in test samples, such as samples of water, food, such as milk, and body fluids. Microorganisms of interest include all aerobic bacteria and specific bacterial groups, such as coliforms. Other microorganisms of interest include a variety of molds and the like.

Classical methods for culturing various microorganisms for detection and identification thereof include the spread plate method, the pour plate method and the liquid medium method. These methods, however, require preparation by technicians. Such preparation includes mixing, heating and pouring, sterilization of culture medium, apparatus, sample spreading etc. before culture of microorganisms, and inoculation of a test sample into the medium.

Particularly in the food industry, testing is very cost-sensitive. In addition, users might not be laboratory-trained technicians. Tests used must, therefore, be user-friendly and inexpensive without sacrificing accuracy.

Applicants desire an alternative user-friendly culture peel plate device, assembly, and method that is useful, for example, for enumeration, detection, identification, and/or transportation of various microorganisms, without the disadvantages of traditional systems and methods.

SUMMARY

In accordance with the present disclosure, peel plates and assemblies are provided for enumeration, detection, and/or identification of various microorganisms. This disclosure provides an improved plate and assembly that is convenient, efficient, and safe for the user.

In one embodiment, an assembly for enumerating a microorganism, when present, includes a recessed well adapted to receive a sample; a raised surface adjacent the recessed well; a dried media culture disc positioned within the recessed well; and a removable moisture barrier having a seal with an adhesive and removably enclosing the recessed well and provide a moisture vapor barrier in an assembled position and less than about one pound peel adhesion.

In some examples, the removable cover seal is removed to receive the sample and reapplied to enclose the recessed well. The sample may be a liquid sample. For instance, the liquid sample may be a liquid extract selected from the group consisting of a solid, a partial solid, and a combination thereof. The assembly may provide less than about two percent liquid moisture loss during incubation.

In another embodiment of the disclosure, a peel plate assembly includes a semi-rigid plate having a recessed well sunken below an upper face, at least one proximate extension adjacent the recessed well, and at least one raised platform adjacent the recessed well; a removable cover seal removably enclosing the recessed well; and an adhesive aligned between the seal and the upper face, and wherein the adhesive provides a moisture vapor barrier in an assembled position and less than about one pound peel adhesion.

In certain examples, the adhesive comprises a solvent acrylic aligned along a perimeter of the recessed well. The adhesive may remove from the upper face without staining. Similarly, the adhesive may remove from the upper face without ghosting. The assembly may comprise about 0.1 to about 0.3 inches of adhesive. For instance, the assembly may comprise about 0.125 inches of adhesive. In some examples, the recessed well includes a grid of a plurality of vertical lines and a plurality of intersecting horizontal lines. Further, the recessed well may receive about five milliliters of sample liquid, while some examples will include greater than five milliliters and some examples will include less than five milliliters of sample liquid.

In another embodiment, in a plate for enumerating a microorganism, when present, having a recessed well and an upper face, a removable moisture barrier includes a seal having a peel tab and removably enclosing the recessed well during storage and incubation; and an adhesive aligned on the seal and adapted to reduce liquid moisture loss from the recessed well.

In some examples, the adhesive bond between the seal and the upper face reduces moisture loss from the recessed well to less than about one percent to about three percent during incubation. For instance, the adhesive bond reduces moisture loss to less than about two percent during incubation.

In certain examples, the removable moisture barrier comprises less than about one pound peel adhesion. The adhesive may provide a stiffness to the seal to allow reapplication of the seal about the plate without wrinkling. The plate may include at least one proximate extension and at least one distal raised platform adjacent the recessed well. Further, the recessed well may include a grid of a plurality of vertical lines and a plurality of intersecting horizontal lines.

Some embodiments of the disclosure for enumerating a microorganism include a recessed well, a raised platform, a dried media culture disc, and a removable cover. Typically, the recessed well receives a sample and the raised platform is adjacent to the recessed well. The dried media culture disc is typically positioned within the recessed well. The removable cover typically includes a first end fixedly secured adjacent to the raised platform, while the opposing second removable end removably encloses the recessed well.

In some examples, the cover's second end includes a peel tab. Further, the removable cover may include an adhesive periphery, for instance on three sides, to removably adhere to an upper face of the plate. The recessed well may be aligned below and parallel to an upper face of the plate. The recessed well may include a grid that is generally visible on the upper face surface and/or lower face surface, for instance for colony counting after the sample has absorbed and diffused throughout the dried media culture disc.

In certain examples, the dried media culture disc supports at least one of (a) an adhesive, (b) a gelling agent, (c) a bacterial nutritive ingredient, (d) a fibrous material, (e) a percent liquid organic solvent, and (f) a cellulosic material. In addition, the plate may include an access indent that is generally opposite the raised platform. The plate may have proximate extensions on opposing sides of the access indent, and the extensions may include an alignment tab.

Another embodiment of the disclosure is a peel plate having a recessed well, a pair of opposing proximate extensions, and a distal raised platform. Typically, the recessed well is spaced between the distal raised platform and the proximate extensions. The recessed well typically has a sunken wall protruding from an upper face. The pair of opposing proximate extensions are typically adjacent to the recessed well, and at least one of the proximate extensions include a proximate tab. The distal raised platform is typically adjacent to the recessed well.

In certain examples, a removable cover encloses the recessed well. The cover may include a peel tab, for instance that is removably secured to a proximate end of the plate. Further, the cover may include a self-wicking adhesive periphery removably adhering to an upper face of the plate. The recessed well may be aligned below and parallel to an upper face of the plate and includes a grid. In particular examples, the grid is visible on the upper face surface and/or lower face surface, for instance for colony counting after the sample has absorbed and diffused. The proximate extensions may be spaced between an access indent. The proximate extensions may each include a rounded corner entry to the access indent. A removable cover may have a peel tab that is generally aligned along the access indent.

In some examples the distal raised platform spans a length of a diameter of the recessed well. Further, a top perimeter may span around the distal raised platform. The distal platform may include a raised edge extending the platform above the top perimeter.

In particular examples, a culture medium is positioned, i.e. secured or the like, in the recessed well. The culture medium may be a dried media culture disc. The dried media culture disc may comprise a bacterial nutritive ingredient. The dried media culture disc may comprise a growth indicator color-developing agent. For instance, the color-developing agent may be triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-bromo-3-indolyl-beta.-D-galactoside, bromothymol blue, and neutral red. Further, the dried media culture disc may comprise a plate count agar or plate count agar individual components. In addition, the dried media culture disc may comprise a yeast and mold growth media. The dried media culture disc may comprise a bacterial nutritive ingredient selective medium for growth of indicator organisms. For example, the bacterial nutritive ingredient may comprise selective growth agents for coliform, *E. coli*, enterbacteriaceae, or pathogens. In addition, the bacterial nutritive ingredient may comprise selective growth agents for *salmonella, listeria*, or camphlobacter.

In some examples, the dried media culture disc comprises an organic solvent. For instance, the organic solvent may comprise a C1-C5 alcohol. In addition, the organic solvent may comprise 2-propanol. The dried media culture disc may comprise an enhancer. Further, the dried media culture disc may comprise a selective agent.

In particular examples, the sample is a liquid sample. For instance, the liquid sample is a liquid extract selected from the group consisting of a solid, a partial solid, and a combination thereof.

In another embodiment of the disclosure, a peel plate includes a recessed well protruding below an upper face; a raised platform that is adjacent the recessed well and extends in an opposing direction from the recessed well; and an adhesive cover removably enclosing the recessed well.

In certain examples the recessed well includes a grid. For instance, the grid may include a plurality of vertical lines and a plurality of intersecting horizontal lines.

In some examples, the raised platform is positioned on a distal portion of the plate and spans a length of a diameter of the recessed well. Further, the raised platform may include a width to support at least one user's finger, or the like. The raised platform may include a raised edge extending away from the upper face. The plate typically includes a top perimeter around the raised platform. The adhesive cover may include a peel tab removably secured to a proximate end of the plate. An access indent may be aligned opposite the raised platform. The access indent may be positioned between opposing proximate extensions. The proximate extensions may include a proximate tab aligning multiple plates in a layered and/or stacked positioned. Typically, the proximate extensions include a rounded corner entry to the access indent.

Yet another embodiment is a method for enumerating microorganisms on a peel plate having a recessed well, a raised platform, a media culture, and an adhesive cover having a tab. The method typically includes at least one of the following: applying pressure with a user's fingers against the raised platform; lifting the tab vertically upward, thereby exposing the recessed well and maintaining coverage of at least a portion of the cover to the plate; dispensing a sample on the media culture; reapplying the adhesive cover to enclose the recessed well; incubating the peel plate; and enumerating the microorganisms, when present, on the media culture.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
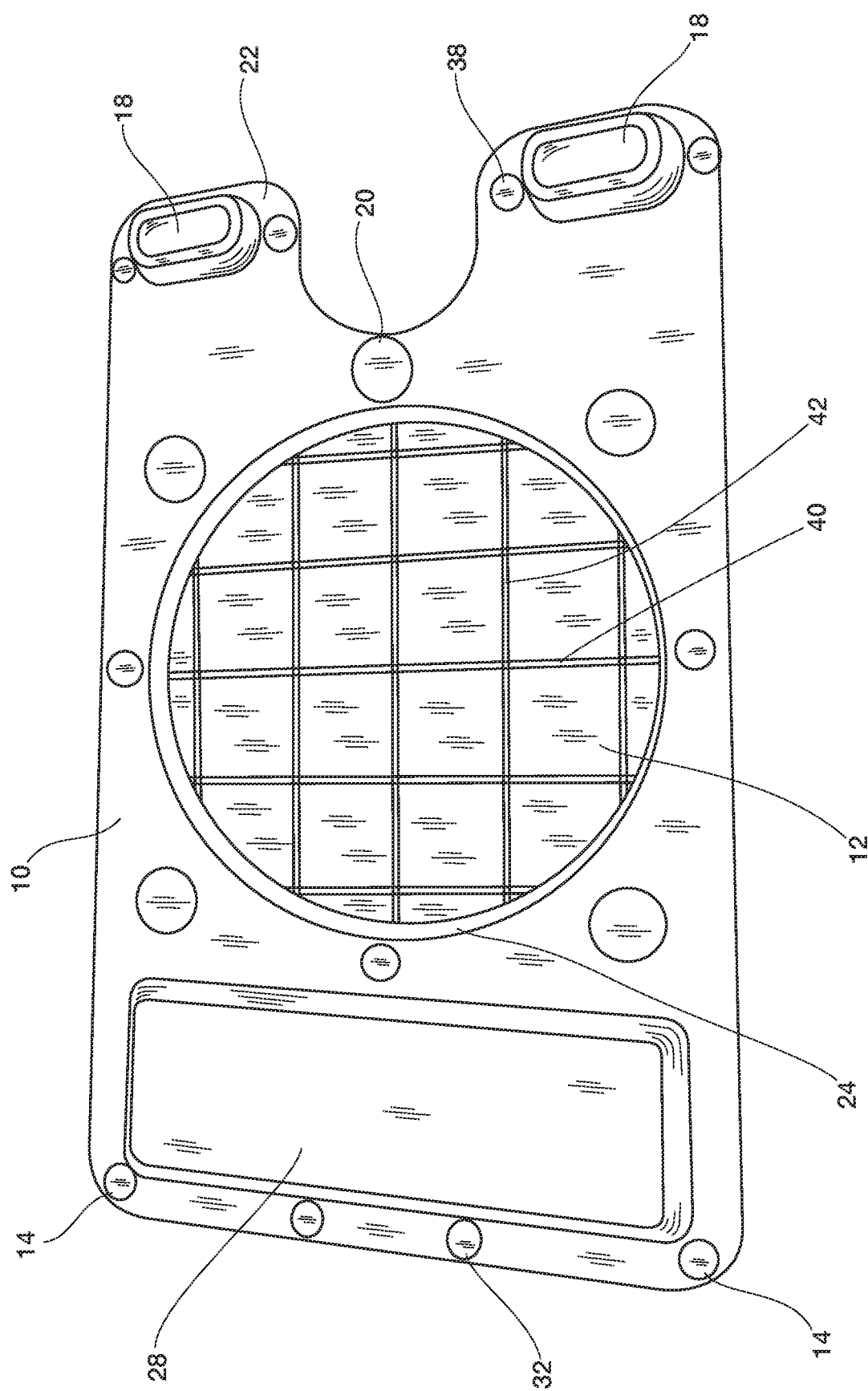
FIG. 1 is a top perspective view of one embodiment of an improved culture peel plate according to the disclosure.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

FIG. 1 introduces one example of a culture device peel plate 10 for enumerating and/or detecting a microorganism from a sample. The peel plate 10 is a semi-rigid waterproof plate onto which sample may be applied to enumerate microorganisms and the like. As seen in FIG. 1, one example of the peel plate 10 includes a recessed well 12, a distal raised platform 28, and opposing proximate extensions 22 having proximate tabs 18 to support stacked plates as shown and described herein. The upper face 14 of the plate typically has a top periphery 32 around the raised platform. The recessed well 12 includes a sunken wall 24 below the upper face 14. As shown in FIG. 1, the recessed well may include a grid, for instance having vertical line 40 and intersecting horizontal line 42 components useful for colony counting. In particular examples, the grid is on the rear surface. In alternative examples, the grid may be printed in a variety of ways, including inkjet printing, pad printing and the like. Regardless of the printing type, the grid is typically visible through the generally transparent culture device to the front surface and/or rear surface. The plate 10 is also typically transparent material so as to enable observation from the outside, including any of the grids shown and described herein.

FIG. 1 further shows the proximate end of the peel plate 10 includes an access indent 20 with opposing proximate extensions 22 between rounded corners 38. Typically, the proximate extensions 22 include proximate tabs 18 for alignment, including, but not limited to, layering and stacking plates.

Figure 2:
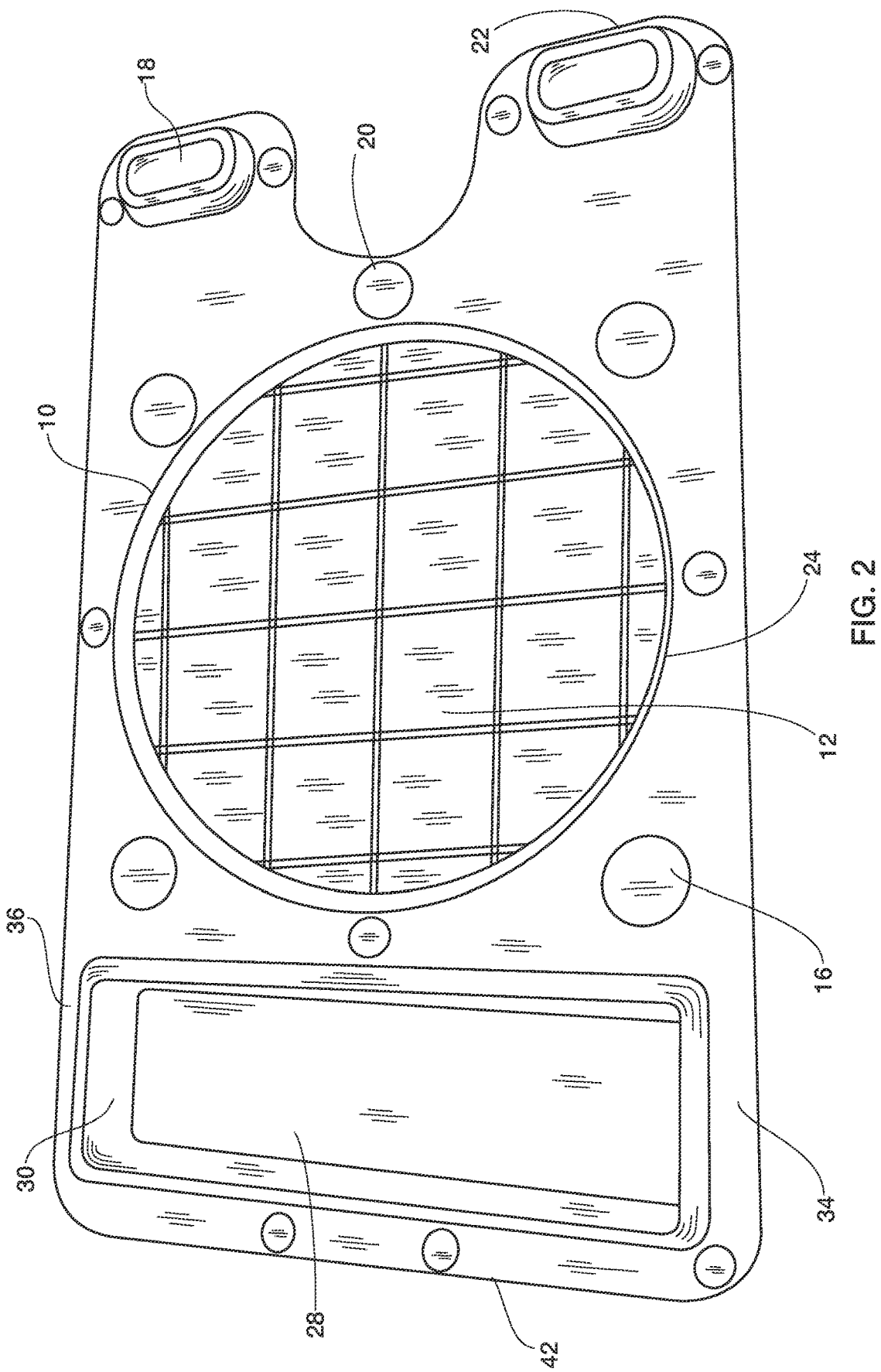
FIG. 2 is a bottom perspective view of the culture plate introduced in FIG. 1.
Figure 3:
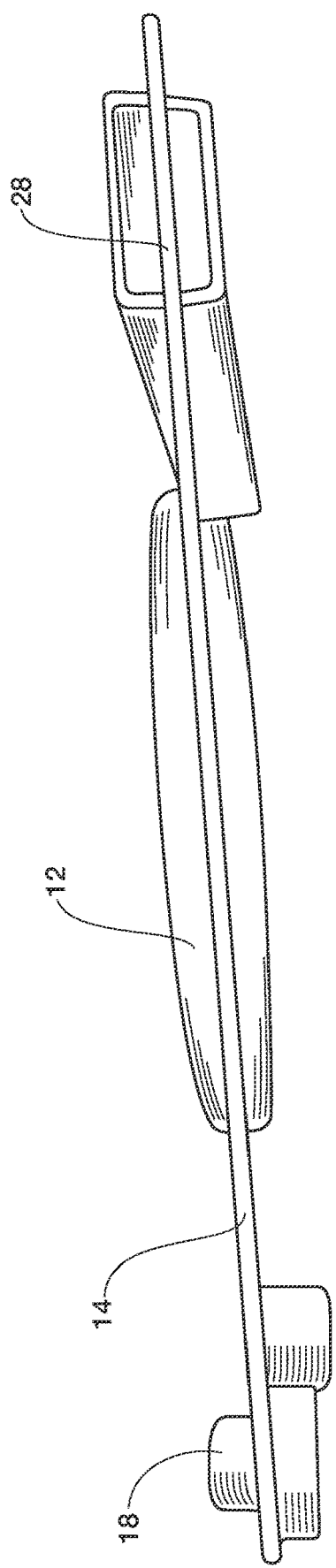
FIG. 3 is a side perspective view of the culture plate introduced in FIG. 1.

FIGS. 2 and 3 show a bottom and side view, respectively, of one example of a peel plate 10 having a raised edge 30 extending above the lower face 16 to define the raised platform 28. Typically, the peel plate has a distal thickness to support any of the elements and testing procedures shown and described herein.

Figure 4:
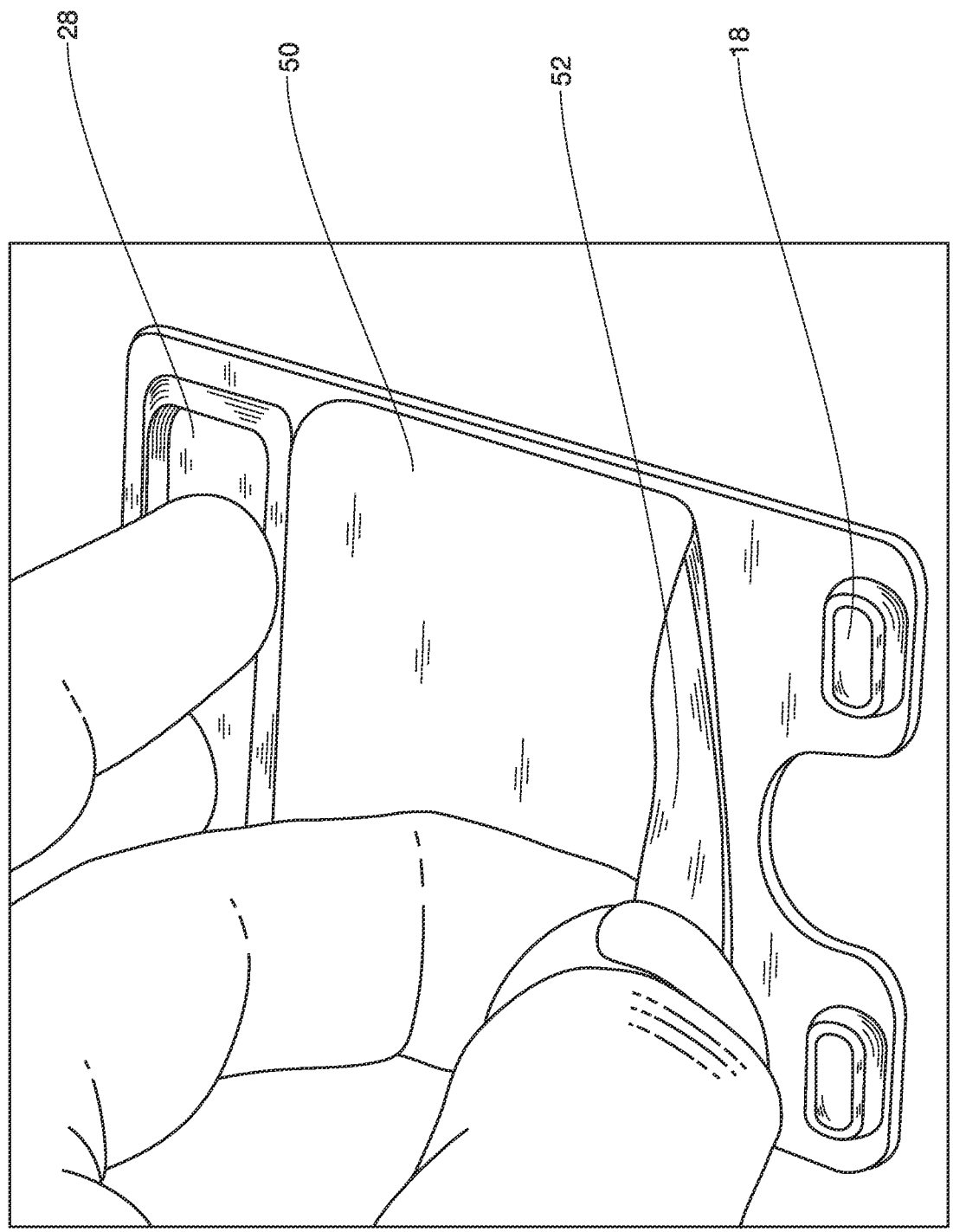
FIG. 4 is one example of a diagnostic procedure utilizing a culture peel plate introduced in FIG. 1.
Figure 5:
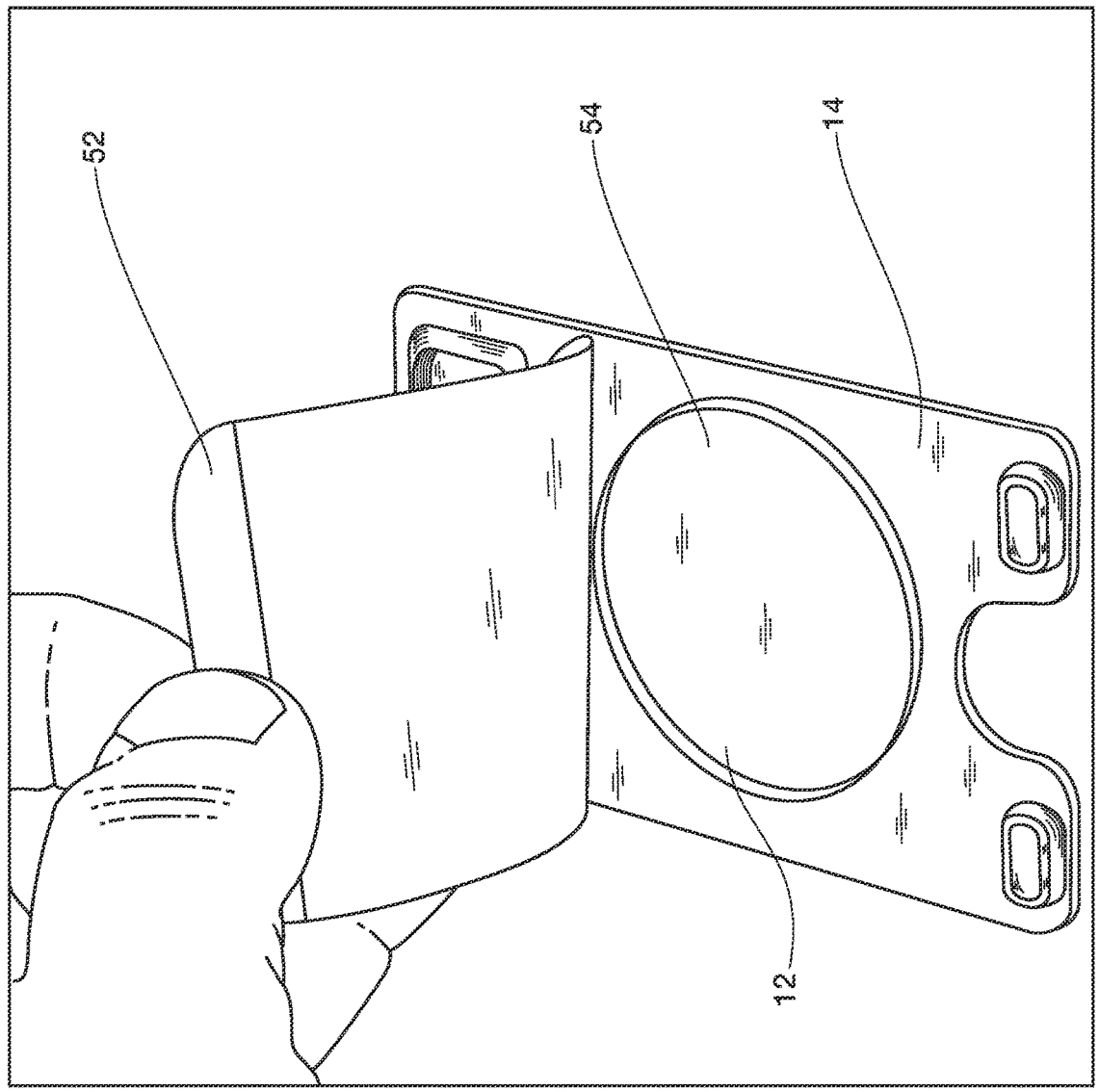
FIG. 5 is another example of a diagnostic procedure utilizing a culture peel plate introduced in FIG. 1.

FIG. 4 introduces certain diagnostic steps for enumerating microorganisms, and the like, from a sample. For instance, the peel plate 10 may be placed on a substantially level surface. The peel tab 52 may be lifted concurrently while pressure is applied to the raised platform 28 with the user's fingers, or the like. As next shown in FIG. 5, the tab 52 is lifted vertically upwards and away to expose the culture media 54. In particular the culture media is any of the dried media culture disc shown and described herein. As shown in FIG. 5, the dried media culture disc 54 secured in the recessed well 12 is generally exposed, but the rear portion of the cover remains affixed to a portion of the upper face 14 of the peel plate 10. For instance, the cover remains affixed to the distal portion of the peel plate 10.

Figure 6:
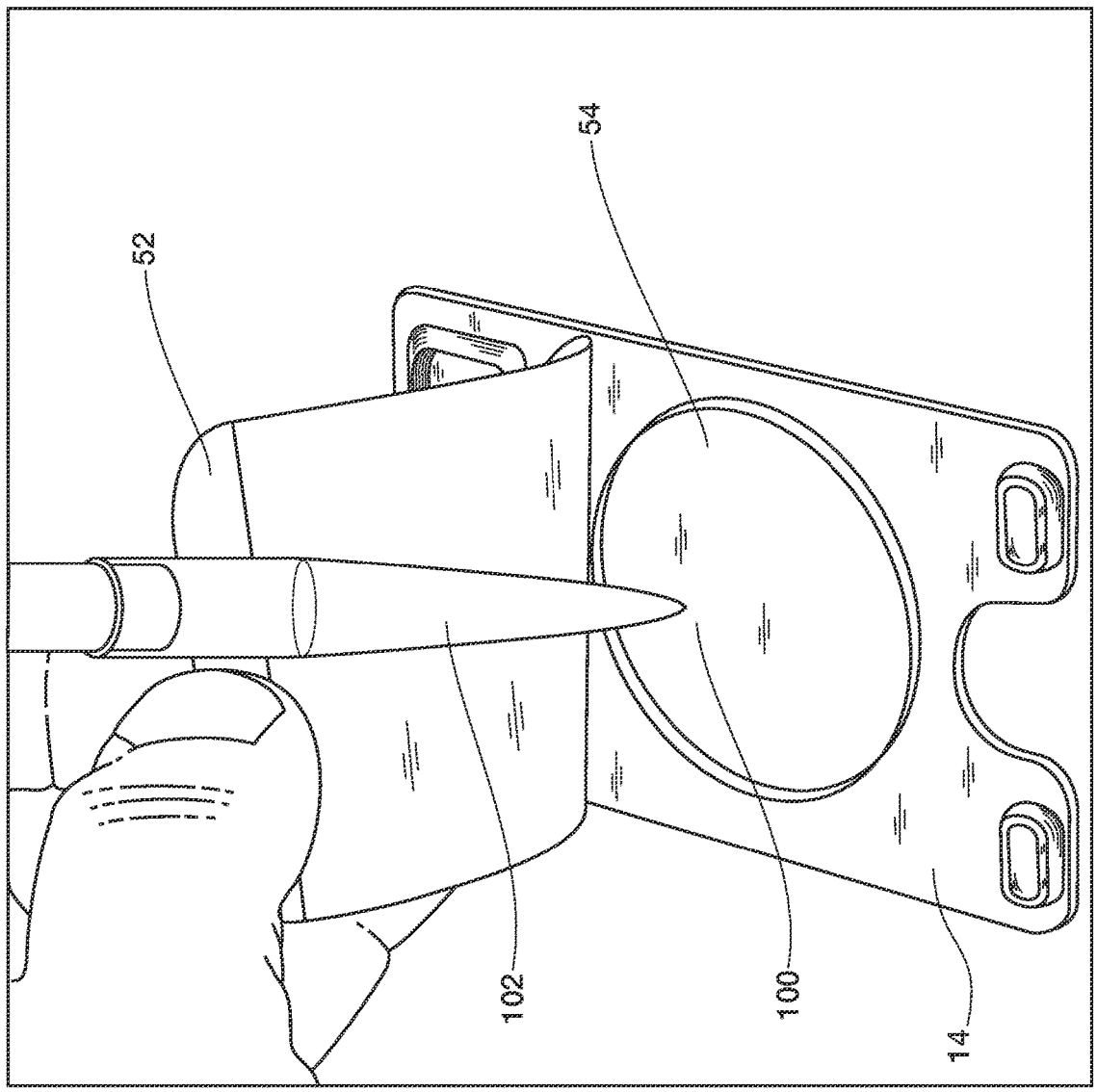
FIG. 6 is a further example of a diagnostic procedure utilizing a culture peel plate introduced in FIG. 1.

FIG. 6 shows one example of dispensing sample 100 to the recessed well. As shown, the peel plate 10 remains on a flat surface and sample 100 is vertically dispensed to the dried media culture disc 54. In particular examples, the sample is expelled from a pipet 102, or similar laboratory tool, rapidly with substantial force and within about two to about three seconds.

Figure 7:
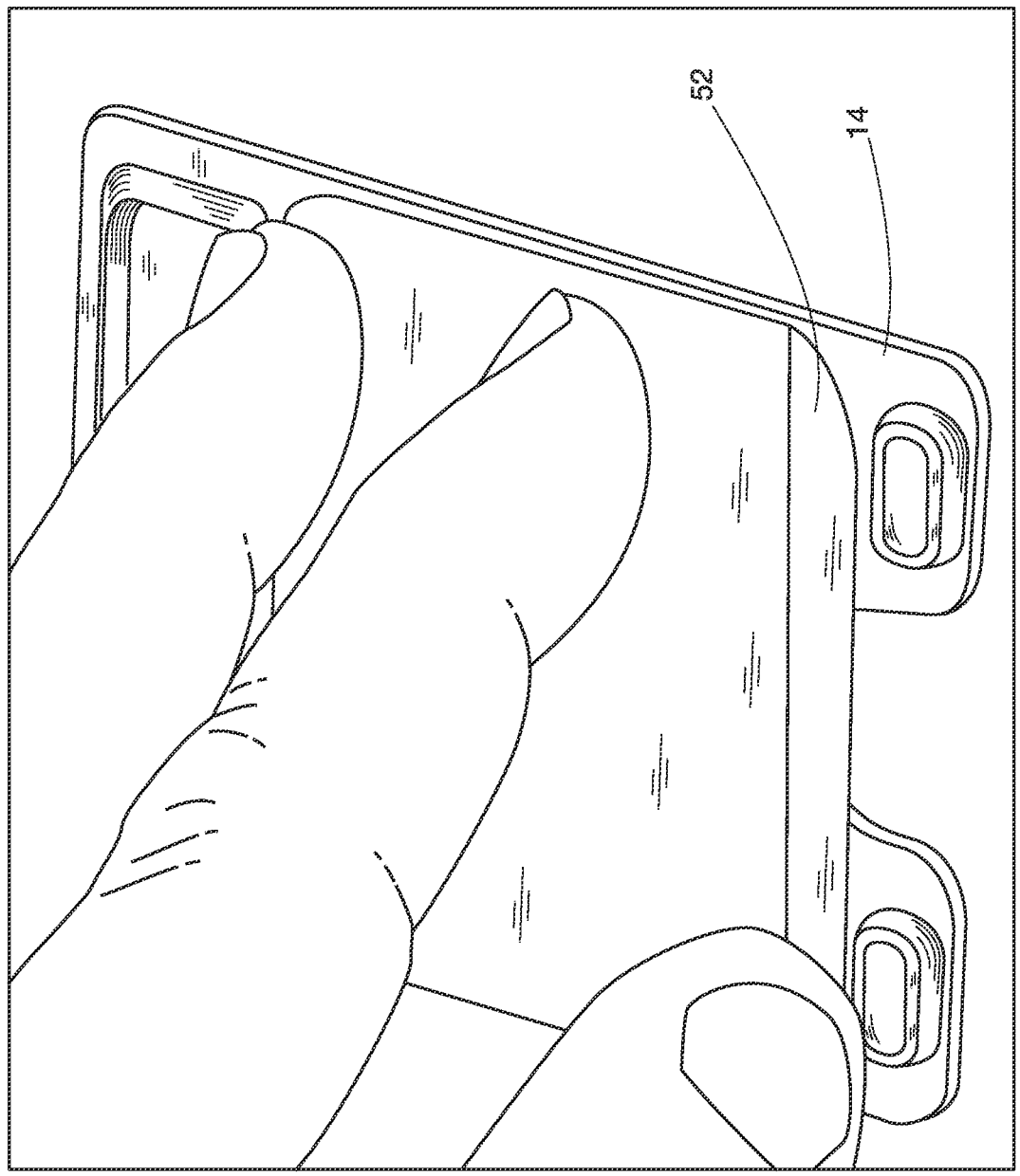
FIG. 7 is yet another example of a diagnostic procedure utilizing a culture peel plate introduced in FIG. 1.

FIG. 7 shows one example of the seal and the adhesive forming the removable moisture barrier as shown and described herein. The adhesive is typically aligned between the cover seal and the upper face 14. For instance, the adhesive may be aligned on the cover seal to provide adhesive strength and stiffness, for instance to allow reapplication of the seal about the plate without wrinkling to expose internal elements as understood by those skilled in the art having the benefit of this disclosure.

In certain examples, the adhesive comprises a solvent acrylic to align with corresponding plate elements, for instance along at least a perimeter of recessed well 12. The removable moisture barrier, including but not limited to the adhesive, may remove from the upper face 14 without staining. Similarly, the removable moisture barrier, including but not limited to the adhesive, may remove from the upper face 14 without ghosting. Further, examples include about 0.1 to about 0.3 inches of adhesive, and Applicants have discovered unexpected benefits of a moisture barrier with about 0.125 inches of adhesive.

In some examples, the adhesive bond between the seal and the upper face 14 reduces moisture loss from recessed well 12 to less than about one percent to about three percent during incubation. For instance, the adhesive bond reduces moisture loss to less than about two percent during incubation. In particular examples, the adhesive is a clear, white, transparent, or the like, ultra removable adhesive and provides improved weather ability and ultra violet resistance.

In particular examples, one or more of the edges of the perimeter of the cover seal may include adhesives as shown and described herein to align with corresponding plate surfaces, for instance by pressing around the edges of the plate to ensure a proper seal. In certain examples, wrinkling the cover may be minimized, or eliminated, by slightly pulling the cover forward while re-applying to the plate.

Figure 8:
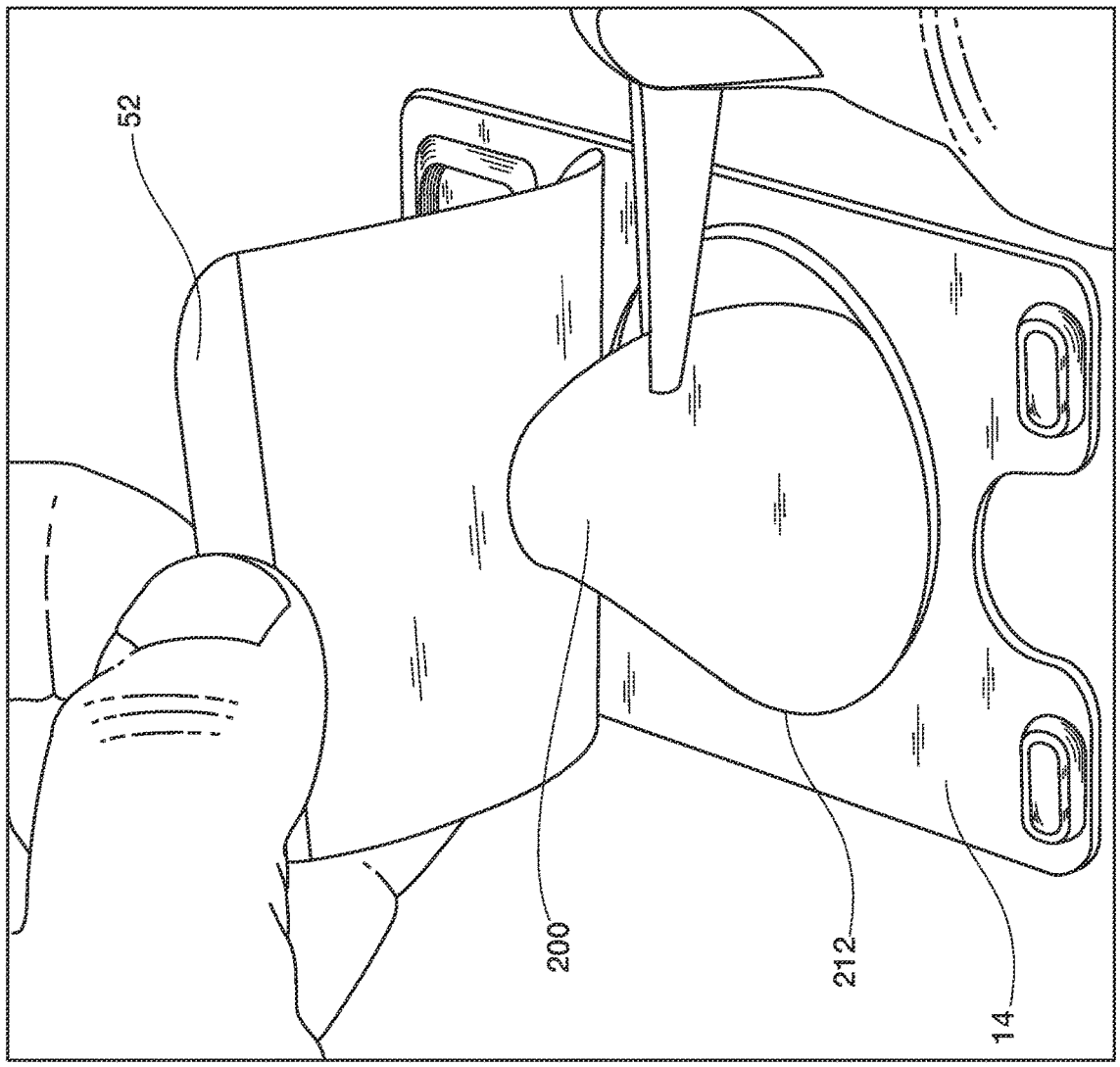
FIG. 8 is one alternative example of a diagnostic procedure utilizing a culture peel plate introduced in FIG. 1.

FIG. 8 shows an alternative embodiment for testing filtered water, wherein the sample is filtered through a mixed cellulose filter membrane 200 in recessed well 212. In particular examples, an aspirator under partial vacuum, a syringe, or the like filters the sample. In these examples, the adhesive cover is lifted to pre-wet a filter with sterile water, or the like before reapplying the adhesive cover.

Figure 9:
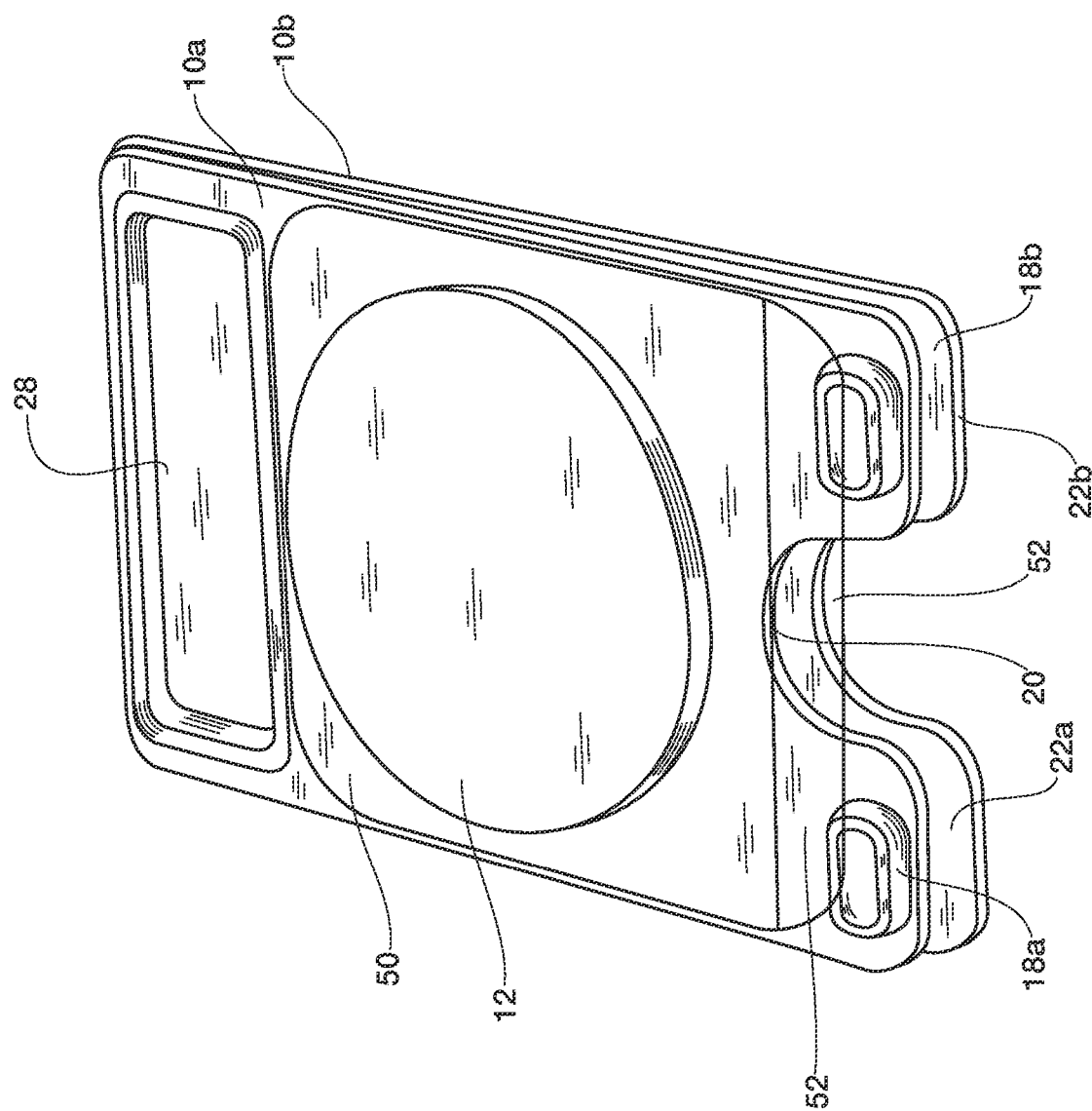
FIG. 9 is a top perspective view of one embodiment of a plurality of stacked culture plates according to the disclosure.

FIG. 9 illustrates one example of layered, or otherwise stacked, peel plates 10a, 10b with aligned proximate tabs 18a, 18b and aligned proximate extensions 22a, 22b as shown and described herein. The stacked arrangement may be incubated as understood by those skilled in the art having the benefit of this disclosure. For instance, the stacked plates may be incubated with their respective adhesive covers 50 down and grid sides aligning upward. Applicants have unexpectedly discovered the plates may be stacked by aligning two pillars and the rectangular platform without affecting plate heat transfer.

General good laboratory practices and precautions should be observed for any of the microbial testing shown and described herein. In certain examples, the peel plate's limit of detection includes one colony forming unit per millimeter (CFU/mL) of sample per filtered sample. Generally, at the end of the diagnostic sequence, including after incubation, the plates may be observed for colony growth, for instance through the bottom side of the plates. In certain examples, one spot may represent one CFU. The sum of the spots may be reported as the CFU/mL or CFH/filtered-water-volume pre sample or sample dilution tested. In particular examples, the filtered samples may be viewed on both the bottom and from the top grid side of the filter, for instance after the adhesive cover is removed. Further, the filter membrane may be viewed under illumination and magnification as understood by those skilled in the art having the benefit of this disclosure to count additional colonies while not reducing TTC or producing other pigments. Still further examples include inserting the peel plate into a reader.

In certain examples, a culture medium mixture may be applied to any of the peel plates shown and described herein The culture medium mixture may include an adhesive; a gelling agent; a bacterial nutritive ingredient; a fibrous material; a percent liquid organic solvent; and a cellulosic material. Typically, wherein upon drying or evaporation of the mixture on the device, the mixture forms a liquid absorbent matrix. The matrix may have a uniform distribution of bacterial growth media that is adapted to absorb and evenly diffuse a liquid sample throughout the absorbent matrix.

In some examples, the gelling agent may be xanthan gum, tica gum, locust bean gum, guar gum, carrageenan, alginate, the like and a combination thereof. The adhesive agent may be hydroxypropylcellulose, hydroxylethylcellulose, solvent soluble cellulosics, the like and a combination thereof. The bacterial nutritive ingredient may comprise EC media. The bacterial nutritive ingredient may comprise plate count agar, plate count agar individual components, the like and a combination thereof. The bacterial nutritive ingredient may comprise yeast and mold growth media. For instance, the bacterial nutritive ingredient may comprise potato dextrose broth.

In particular examples, the bacterial nutritive ingredient may comprise selective medium for growth of indicator organisms. For instance the bacterial nutritive ingredient may comprise growth promoters for bacteria such as coliform, *E. coli*, enterobacteriaceae, or pathogens. The bacterial nutritive ingredient may comprise growth promoters for pathogens, such as *salmonella, listeria*, or camphlobacter.

In some examples, the organic solvent comprises ethanol, isopropyl alcohol, the like and a combination thereof. The alcohol percentage may be more than about 50%, including about 60-80%. The organic solvent may contain a percentage of water. The water percentage may be about 1-30%, greater than about 10%, about 15-20% or the like.

The medium may further comprise a growth indicator color-developing agent. In some examples, the color-developing agent includes at least one of the following: triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-bromo-3-indolyl-beta.-D-galactoside, bromothymol blue, and neutral red. The color-developing agent may include triphenyltetrazolium chloride.

In some examples, the organic solvent comprises a C1-C5 alcohol. In yet other examples, the organic solvent comprises 2-propanol. The medium mixture may include a selective agent. The selective agent may comprise SDS. For instance, the selective agent may comprise bile salts, deoxycholate, sodium citrate or other gram negative selective agents.

Additional medium mixture examples include an enhancer. The enhancer may comprise isopropyl-β-D-thiogalactoside (IPTG) or another similar analogue to lactose. A color enhancer may comprise x-gal.

In particular examples, the fibrous material comprises Rayon, a Rayon derivative, the like or a combination thereof. The fibrous material may include cellulose acetate. Further, the fibrous material may comprise trilobal Rayon. In certain examples, the fibrous material comprises Rayon and wherein the Rayon has a weight of denier filament in the range of about 0.2 mm to about 1.0 mm. For instance the fibrous material comprises Rayon and wherein the Rayon has a denier per filament of about 0.8 to about 3.0.

The selective bacterial nutritive ingredient may comprise components of EC media. The adhesive may comprise polyvinyl pyrrolidone. In other examples the adhesive comprises polyethylene oxide.

In certain examples, the liquid sample is a liquid extract of solid, a partial solid, and a combination thereof.

Another example of the present disclosure includes a colloidal slurry matrix free of a mesh or weave in any of the peel plates shown and described herein. For instance, in a peel plate device for detecting a microorganism, when present, in a liquid sample, a colloidal slurry matrix free of a mesh or weave may include an adhesive; a gelling agent; a bacterial nutritive ingredient; a plurality of Rayon fiber particles; a percent liquid organic solvent; and cellulosic material. Typically, the matrix is a liquid absorbent matrix having a uniform distribution of bacterial growth media that is generally adapted to absorb and evenly diffuse the liquid sample throughout the matrix.

In certain examples, a culture medium and method for detecting microorganisms in a sample, such as a milk sample, a water sample or other food sample, comprising a mixture that can include an adhesive, a gelling agent, a bacterial nutritive ingredient, a fibrous material, a percent liquid organic solvent, and cellulosic material. Upon addition to a waterproof and flat device and being allowed to dry or evaporate the liquid, the mixture forms a bacterial growth media-infused, liquid absorbent and diffusing, matrix that is adhered to the base of the waterproof and flat device.

The gelling agent can be, for example, one or more of tica gum, xanthan gum, locust bean gum, guar gum, carrageenan, or alginate. The adhesive, when present, can be, for example, one or more of KLUCEL (hydroxypropylcellulose), a solvent soluble cellulosic, for instance carboxymethylcellulose, polyvinyl pyrrolidone and polyethylene oxide. The culture medium bacterial nutritive ingredient can be, for example, EC media or one or more of its individual components thereof or other media and media components known in the art. In other examples, the bacterial nutritive ingredient can be plate count agar or its individual components. The culture medium can also include one or more growth indicator color-developing agents such as triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-Bromo-4-Chloro-3-Indolyl-B-D-glucuronide; 6-Chloro-3-Indolyl-B-D-galactopyranoside; 5-bromo-3-indolyl-.beta.-D-galactoside, bromothymol blue, and neutral red. The organic solvent can include one or more of ethanol and isopropyl alcohol and can also include, in some aspects, a percentage of water, for example 1-30% water, more than 10% water or in the range of 15-20% water.

In other examples, the solvent can also include one or more alcohols, for example more than 50% or in the range of about 60% to about 80%. Useful alcohols include C1-C5 alcohols such as 2-propanol and ethanol. The waterproof flat plate can be made of, for example, plastic or glass and can be in a typical Petri dish configuration or in a clamshell-like configuration as shown in FIG. 1, and may also include PET plastics, polypropylene, polypropylene and the like. The culture medium can also include an enhancer such as IPTG or another similar analogue to lactose. The fibrous material can include materials such as Rayon or Rayon derivatives or similar materials such as trilobal Rayon, which can be used with a hydrophilic cellulose ester, such as cellulose acetate. The culture medium can also include one or more selective agents such as SDS, antibiotics, deoxycholate, citrate and/or bile salts.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. A peel plate assembly comprising:

a. a semi-rigid plate having a recessed well that is sunken below an upper face, wherein a bottom wall of the recessed well on a lower horizontal plane below said upper face, a pair of proximate extensions extending radially and being offset from said lower horizontal plane of said recessed well and independent of said recessed well, and wherein each of said proximate extensions having a tab adjacent said upper face and protruding from said proximate extensions, and at least one raised platform protruding from said upper face and on an upper horizontal plane spaced offset from said lower horizontal plane of said recessed well and independent of said adjacent recessed well;

b. a removable cover seal having a perimeter and aligned between said protruding proximate extensions and said protruding raised platform, thereby removably enclosing said recessed well; and c. an adhesive aligned between said pair of proximate extensions and between said removable cover seal and said upper face, and wherein said adhesive provides a moisture vapor barrier along said perimeter around said recessed well in an enclosed position and less than one pound peel adhesion.

2. The peel plate assembly of claim 1, wherein said adhesive comprises a solvent acrylic aligned along a perimeter of said recessed well.

3. The peel plate assembly of claim 2, wherein said adhesive adapted to be removed from said upper face without staining.

4. The peel plate assembly of claim 2, wherein said adhesive adapted to be removed from said upper face without ghosting.

5. The peel plate assembly of claim 1, wherein said assembly comprises about 0.1 to about 0.3 inches of adhesive.

6. The peel plate assembly of claim 5, wherein said assembly comprises about 0.125 inches of adhesive.

7. The peel plate assembly of claim 1, wherein said recessed well includes a grid of a plurality of vertical lines and a plurality of intersecting horizontal lines.

8. The peel plate assembly of claim 1, wherein said recessed well being adapted to receive about five milliliters of sample liquid.

\* \* \* \* \*